United States Patent
Arsenault et al.

(10) Patent No.: US 10,401,316 B2
(45) Date of Patent: Sep. 3, 2019

(54) ACOUSTIC EVENT MONITORING FOR TRIGGERING OF HEALTH SCAN OF A STRUCTURE

(71) Applicant: Simmonds Precision Products, Inc., Vergennes, VT (US)

(72) Inventors: Tyler Arsenault, Charlotte, VT (US); Peter J. Carini, Underhill, VT (US)

(73) Assignee: Simmonds Precision Products, Inc., Vergennes, VT (US)

(*) Notice: Subject to any disclaimer, the term of this patent is extended or adjusted under 35 U.S.C. 154(b) by 179 days.

(21) Appl. No.: 15/603,156

(22) Filed: May 23, 2017

(65) Prior Publication Data
US 2018/0340898 A1 Nov. 29, 2018

(51) Int. Cl.
*G01N 25/72* (2006.01)
*G01N 29/24* (2006.01)
(Continued)

(52) U.S. Cl.
CPC ............ *G01N 25/72* (2013.01); *B64F 5/60* (2017.01); *G01H 9/004* (2013.01);
(Continued)

(58) Field of Classification Search
CPC ............ G01N 25/72; G01N 29/2418; G01N 2291/2694; B64F 5/60; G01H 9/004;
(Continued)

(56) References Cited

U.S. PATENT DOCUMENTS

| 5,026,140 A | 6/1991 | Russom |
| 6,204,920 B1 * | 3/2001 | Ellerbrock ......... G01D 5/35383 250/227.13 |

(Continued)

FOREIGN PATENT DOCUMENTS

KR 20130075065 A 7/2013

OTHER PUBLICATIONS

Jae-Hoon Song, Implementation of Sensor-embedded Main Wing Model of Ultra Light Airplane for Health and Usage Monitoring System (HUMS) Test-bed, Oct. 17-21, 2012, 3 pages, Jeju Island, Korea.

(Continued)

*Primary Examiner* — Lisa M Caputo
*Assistant Examiner* — Philip L Cotey
(74) *Attorney, Agent, or Firm* — Kinney & Lange, P.A.

(57) ABSTRACT

Apparatus and associated methods relate to generating a trigger signal in response to detection of a triggering acoustic event sensed by one of a distributed network of optical acoustic sensors mechanically coupled to an aircraft structure. Each of the optical acoustic sensors is configured to generate an optical response signal indicative of an acoustic condition detected by the optical acoustic sensor. A controller receives the optical response signals and generates, if a triggering one of the optical response signals is indicative of a triggering acoustic event, a trigger signal. The controller also determines a location of the specific one of the distributed network of optical acoustic sensors that generated the triggering one of the optical response signals. In some embodiments, the trigger signal is sent to a Health & Usage Monitoring System configured to perform a health scan, in response to receiving the trigger signal, of the aircraft structure.

20 Claims, 4 Drawing Sheets

(51) Int. Cl.
    *B64F 5/60*     (2017.01)
    *G01H 9/00*     (2006.01)
    *G01M 5/00*     (2006.01)
    *G01M 11/08*     (2006.01)

(52) U.S. Cl.
    CPC ........ *G01M 5/0016* (2013.01); *G01M 5/0066* (2013.01); *G01M 5/0091* (2013.01); *G01M 11/085* (2013.01); *G01N 29/2418* (2013.01); *G01N 2291/2694* (2013.01)

(58) Field of Classification Search
    CPC ............. G01M 5/0016; G01M 5/0066; G01M 5/0091; G01M 11/085
    See application file for complete search history.

(56) References Cited

U.S. PATENT DOCUMENTS

| | | | |
|---|---|---|---|
| 6,564,640 B1* | 5/2003 | Allaei | F16F 15/00 |
| | | | 73/583 |
| 6,930,820 B1 | 8/2005 | Shooks, Jr. et al. | |
| 7,075,424 B1* | 7/2006 | Sundaresan | G01N 29/14 |
| | | | 340/500 |
| 7,729,035 B2 | 6/2010 | Kim | |
| 8,534,133 B2* | 9/2013 | Hucker | B29C 70/10 |
| | | | 73/777 |
| 10,024,756 B2* | 7/2018 | Da Silva | G01M 5/0033 |
| 2009/0157358 A1* | 6/2009 | Kim | G01L 1/16 |
| | | | 702/185 |
| 2011/0170823 A1* | 7/2011 | Xia | G01D 5/35303 |
| | | | 385/12 |
| 2015/0247826 A1* | 9/2015 | Soejima | G01N 29/2418 |
| | | | 73/643 |
| 2015/0338344 A1* | 11/2015 | Carralero | G01D 5/268 |
| | | | 250/227.23 |
| 2016/0116366 A1* | 4/2016 | Da Silva | G01M 5/0033 |
| | | | 702/35 |
| 2016/0340058 A1* | 11/2016 | Da Silva | B64D 45/00 |
| 2017/0168021 A1* | 6/2017 | Van Tooren | G01N 29/041 |

OTHER PUBLICATIONS

Jinsik Yun, Development of Structural Health Monitoring Systems Incorporating Acoustic Emission Detection for Spacecraft and Wind Turbine Blades, Apr. 28, 2011, 45 pages, Blacksburg, VA.

M. Scheerer, T. Cardone, A. Rapisarda, S. Ottaviano and D. Francesconi, Online Damage Detection on Metal and Composite Space Structures by Active and Passive Acoustic Methods, 9 pages.

Extended European Search Report dated Nov. 7, 2018 for corresponding EP Application No. 18173721.4.

* cited by examiner

ACOUSTIC EVENT MONITORING FOR TRIGGERING OF HEALTH SCAN OF A STRUCTURE

BACKGROUND

During the operation of an aircraft, numerous on-board components and subsystems are continuously or periodically monitored. Various methods for monitoring these components and sub-systems of the aircraft have been used. For example, sensors and/or transducers can be mechanically affixed to an aircraft at specific locations so as to produce signals indicative of various physical phenomena experienced at those specific locations. In some embodiments, to interrogate structures of concern, one or more transducers can generate an acoustic signal and couple the generated acoustic signal to the aircraft at the specific location(s) at which the one or more transducers are affixed. Additionally, acoustic sensors can be affixed to locations of the aircraft and then can sense the acoustic condition at the affixed locations and generate signals indicative of the sensed acoustic condition. These signals can then be transmitted to an analyzer that interprets the signals received by the analyzer.

The analyzer can then compare the received signals indicative of the sensed acoustic condition with baseline and/or reference signals. If the sensed acoustic signals are sufficiently different from the baseline and/or reference signals, the analyzer can generate an alert signal and/or control the transducers so as to perform a more detailed probing of the acoustic condition of the aircraft to monitor the health of the aircraft. Such health monitoring scans can take a long time to perform if much detailed information is required. Such detailed health monitoring scans can require high power and/or energy to complete.

Optical sensors and/or transducers can produce optical signals indicative of various physical phenomena, and with low power requirements. For example, optical sensors and/or transducers can produce optical signals indicative of stress, strain, temperature, tilt, rotation, vibration, pressure, etc. Various sensors and/or transducers employ various types of technologies. For example, some sensors use Fabry-Pérot Interferometry (FPI). Some sensors use Fiber Bragg Grating (FBG) technologies. Some sensors use intensity modulation techniques. Some of these technologies and techniques produce optical signals having a spectrum that is indicative of the measured parameter. This disclosure is directed to the use of a distributed network of optical sensors for monitoring and/or sensing the acoustic condition of an aircraft structure, impacts to that structure, and for triggering a health monitor scan in response to the sensed acoustic condition.

SUMMARY

Apparatus and associated methods relate to a system for monitoring health of an aircraft structure. The system includes an optical emitter, a series of optical acoustic transducers, and an optical detector all optically coupled to an optical fiber network extending along an aircraft structure. The optical emitter optically is configured to generate an optical signal and to transmit the generated optical signal to the optical fiber network. The series of optical acoustic transducers is mechanically coupled to the aircraft structure at a series of acoustic sensor locations. Each of the series of optical acoustic transducers is configured to receive the generated optical signal, to generate an optical response signal indicative of a detected acoustic condition at the acoustic sensor location at which the optical acoustic transducer is coupled, and to transmit the generated optical response signal to the optical fiber network. The optical detector is configured to receive the transmitted optical response signals generated by the series of optical acoustic transducers. The system also includes a controller configured to generate a trigger signal, if a triggering one of the received optical response signals is indicative of a triggering acoustic event. The controller is further configured to determine, based on a relative timing of the triggering one of the received optical response signals, a specific one of acoustic sensor locations associated with a specific one of the series of optical acoustic transducers that generated the triggering one of the optical response signals associated with the generated trigger signal.

Some embodiments relate to a method for monitoring health of an aircraft structure. The method includes extending an optical fiber network along an aircraft structure. Then, an optical signal is generated and transmitted to the optical fiber network. Acoustic conditions at a series of acoustic sensor locations along the optical fiber network are then detected via a series of optical acoustic transducers mechanically coupled to the aircraft structure at the series of acoustic sensor locations. Then, the transmitted optical signal is received via the series of optical acoustic transducers. In response to receiving the transmitted optical signal via the series of optical acoustic transducers, optical response signals indicative of the detected acoustic conditions are generating. Then, the generated optical response signals to the optical fiber network are transmitted via the series of optical acoustic transducers. The transmitted optical signals are received via an optical detector. Then, if a triggering one of the received optical response signals is indicative of a triggering acoustic event, a trigger signal is generated via a controller. Based on a relative timing of the triggering one of the received optical response signals via the controller, a specific one of acoustic sensor locations associated with a specific one of the series of optical acoustic transducers that generated the triggering one of the optical response signals associated with the generated trigger signal is determined.

DETAILED DESCRIPTION

Apparatus and associated methods relate to generating a trigger signal in response to detection of a triggering acoustic event sensed by one of a distributed network of optical acoustic sensors mechanically coupled to an aircraft structure. Each of the optical acoustic sensors is configured to generate an optical response signal indicative of an acoustic condition detected by the optical acoustic sensor. A controller receives the optical response signals and generates, if a triggering one of the optical response signals is indicative of a triggering acoustic event, a trigger signal. The controller also determines a location of the specific one of the distributed network of optical acoustic sensors that generated the triggering one of the optical response signals. In some embodiments, the trigger signal is sent to a Health & Usage Monitoring System (HUMS) configured to perform a health scan, in response to receiving the trigger signal, of the aircraft structure.

Figure 1:
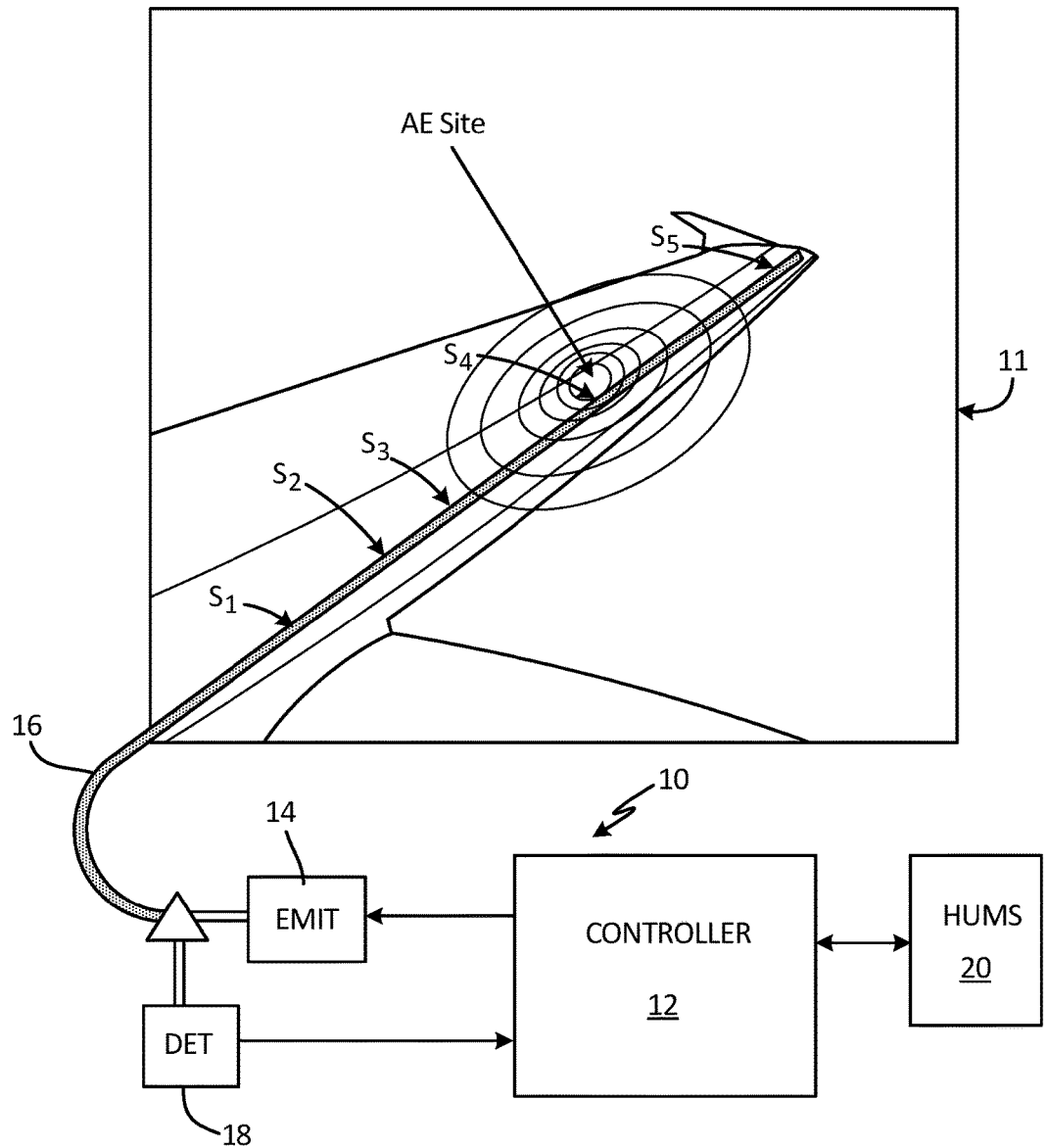
FIG. 1 is a schematic diagram of an exemplary system for monitoring acoustic events over a distributed network of optical acoustic sensors.

FIG. 1 is a schematic diagram of an exemplary system for monitoring acoustic events over a distributed network of optical acoustic sensors. In FIG. 1, Acoustic event detection system 10 is monitoring aircraft structure 11. Acoustic event detection system 10 includes controller 12, optical emitter 14, optical fiber network 16, optical acoustic sensors $S_1$-$S_N$, optical detector 18, and Health & Usage Monitoring System (HUMS) 20. Optical acoustic sensors $S_1$-$S_N$ are optically coupled to optical fiber network 16 and are mechanically coupled to aircraft structure 11 at various sensor locations along optical fiber network 16. Each of optical acoustic sensors $S_1$-$S_N$ can be external to optical fiber network 16 or can be formed within optical fiber network 16. Each of optical acoustic sensors $S_1$-$S_N$ can generate and/or affect an optical signal in indicative of an acoustic condition of the sensor location at which the sensor is mechanically coupled to aircraft structure 11. In some embodiments, sensors $S_1$-$S_N$ can be formed within optical fiber network 16 as Fiber Bragg Gratings (FBG). In some embodiments, for example, sensors can be Fabry-Pérot Interferometers (FPI) external but optically coupled to optical fiber network 16.

For example, in some embodiments, controller 12 sends a control signal to optical emitter 14. In response to receiving the control signal from controller 12, optical emitter 14 generates a pulse of optical energy and directs the generated pulse into optical fiber network 16. Optical fiber network 16 receives the generated pulse of optical energy and transmits the received pulse of optical energy to optical acoustic sensors $S_1$-$S_N$ distributed along optical fiber network 16. Optical fiber network 16 conducts the generated pulse of optical energy and guides it to each of optical acoustic sensors $S_1$-$S_N$. Because the pulse of optical energy travels within optical fiber network 16 at a speed no greater than the speed of light, optical acoustic sensors $S_1$-$S_N$ encounter and/or receive the pulse of optical energy in the order in which optical acoustic sensors $S_1$-$S_N$ are distributed along optical fiber network 16.

As each of optical acoustic sensors $S_1$-$S_N$ encounters the transmitted pulse of optical energy, a portion of the encountered pulse of optical energy is reflected by optical acoustic sensors $S_1$-$S_N$. The portion of the pulse of optical energy reflected by each of the optical acoustic sensors $S_1$-$S_N$ is indicative of the acoustic condition at the reflecting sensor location sensed by the reflecting optical acoustic sensor $S_1$-$S_N$. The portion of the pulse of optical energy reflected by each of optical acoustic sensors $S_1$-$S_N$ can be of a narrow band of wavelengths and/or be characterized by a specific wavelength. That specific wavelength and/or narrow-band of wavelengths can be indicative of the sensed acoustic condition. In some embodiments, as each of optical acoustic sensors encounters the transmitted pulse of optical energy, the optical acoustic sensor generates an optical signal indicative of the acoustic condition at the generating sensor location. In some embodiments, the sensors generate an optical signal indicative of the acoustic condition at the generating sensor location independent of a transmitted pulse of optical energy.

Optical detector 18 then receives and detects the portions of the pulse of optical energy reflected by optical acoustic sensors $S_1$-$S_N$. Optical detector 18 outputs a signal indicative of the detected portions of the pulse of optical energy reflected by optical acoustic sensors $S_1$-$S_N$. Controller 12 receives the signal output by optical detector and processes the output signal, so as to determine the acoustic conditions sensed by optical acoustic sensors $S_1$-$S_N$. Controller 12 associates each of the portions of the pulse of optical energy reflected by each of the optical acoustic sensors $S_1$-$S_N$ with the specific one of the optical acoustic sensors $S_1$-$S_N$ that generated that portion. Controller 12 can associate portions of the detected signal corresponding to portions of the pulse of optical energy reflected by each of the optical sensors $S_1$-$S_N$ with each optical acoustic sensor $S_1$-$S_N$ based on the time difference between the time that the pulse of optical energy is generated by optical emitter 14 and the time that the specific reflected portion is detected by optical detector 18. In some embodiments, controller 12 can associate each specific reflected portion with each optical acoustic sensor $S_1$-$S_N$ based on wavelengths of the detected portions.

If one of the reflected portions is indicative of a triggering acoustic event controller 12 generates a trigger signal. Controller 12, for example, can compare each of the reflected portions with a baseline signal and/or a reference signal. If one of the reflected portions is too dissimilar in some way from the baseline signal and/or the reference signal, controller 12 identifies the dissimilar reflected portion as a triggering one of the reflected portions. The triggering one of the reflected portions is indicative of a triggering acoustic event. A triggering acoustic event, for example, could be an acoustic event having a magnitude that exceeds a predetermined threshold. In some embodiments, a triggering acoustic event could be an acoustic event having a frequency of oscillation exceeding a predetermined threshold. Such triggering acoustic events might be caused, for example by debris and/or a bird striking aircraft structure 11, and/or vibration due to a loose and/or broken part.

In some embodiments, HUMS 20 receives the trigger signal, and in response initiates a scan of aircraft structure 11. In some embodiments HUMS 20 performs an active scans of aircraft structure 11 at and near sensor locations associated with the trigger signal. In some embodiments, HUMS 20 can perform a full scan of aircraft structure 11, in response to receiving a trigger signal. HUMS 20, for example, can include one or more acoustic sensors for actively monitoring acoustic signals. HUMS 20 can be further configured to compare the monitored acoustic signals to a baseline acoustic signal(s).

In some embodiments, instead of or in addition to HUMS 20, a Structural Health Monitoring (SHM) system can be used. The SHM system can include both active acoustic transducers and acoustic sensors. The active acoustic transducers can be configured to actively generate acoustic signals. The acoustic sensors can be configured to detect acoustic responses to the actively generated acoustic signals. The SHM system can be configured to compare the detected acoustic responses with a baseline response. The SHM system can be configured to perform such a SHM scan in response to receiving a trigger signal.

Figure 2:
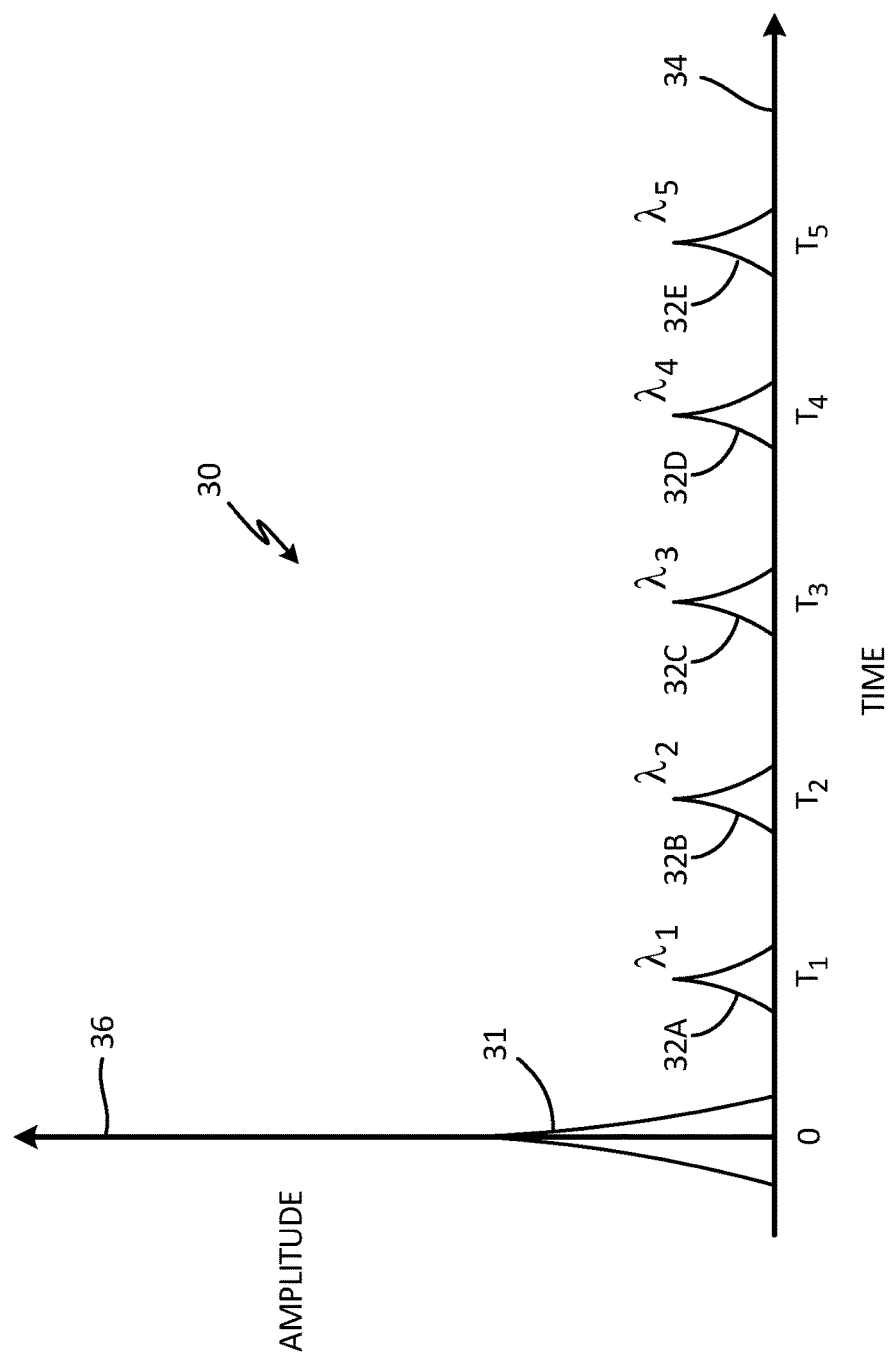
FIG. 2 is a graph of a sequence of optical pulses backscattered from sensors distributed along a loop of an optical fiber.

FIG. 2 is a graph of a sequence of optical pulses backscattered from optical acoustic sensors distributed along a loop of an optical fiber. In FIG. 2, graph 30 depicts pulse 31 of optical energy emitted by optical emitter 14 (shown in FIG. 1) and a train of optical pulses 32A-32E generated by sensors $S_1$-$S_5$ (also shown in FIG. 1). Graph 30 includes horizontal axis 34, which is indicative of time. Graph 30 also include vertical axis 36, which is indicative of amplitude. Because sensor $S_1$ is located closest to controller 12, optical pulse 32A is the first to be received by controller 12 after pulse 31 is emitted by emitter 14. Because sensor $S_2$ is located next closest to controller 12, optical pulse 32B is the second to be received by controller 12. In this way, controller 12 can associate each of optical pulses 32A-32E with sensors $S_1$-$S_5$, respectively, based on the time delay between the initial emission of generated optical pulse 31 and detection of the reflected optical pulses 32A-32E.

The emitted pulse 31 of optical energy can have a domain of wavelengths that includes all wavelengths to which sensors $S_1$-$S_5$ are responsive. Each of reflected optical pulses 32A-32E can have a specific wavelength and/or a narrow-band of wavelengths as indicated in graph 30 by $\lambda_1$-$\lambda_5$. For example, each of sensors $S_1$-$S_5$ can be a FBG-type of sensor with a spatial grating frequency that is unique to each sensor. Having unique grating frequencies permits the frequency to which each sensor is responsive to be transmitted through other FBG-type sensors without reflection. In some embodiments, optical fiber network includes a series of optical fibers. Each of the series of optical acoustic sensors is optically coupled to a respective optical fiber. In such embodiments, FBG-type sensors can all have the same spatial grating frequency.

As optical pulses 32A-32E are received by controller 12 (depicted in FIG. 1), a spectrum analyzer can determine the corresponding specific wavelengths or narrow-band of wavelengths $\lambda_1$-$\lambda_5$, respectively. The determined wavelengths of the optical pulses 32A-32E can be indicative of the acoustic condition measured by sensors $S_1$-$S_5$, respectively. Optical acoustic sensors can be distributed at small intervals along optical fiber network 16 (depicted in FIG. 1), thereby facilitating precise location of a triggering acoustic event.

Figure 3:
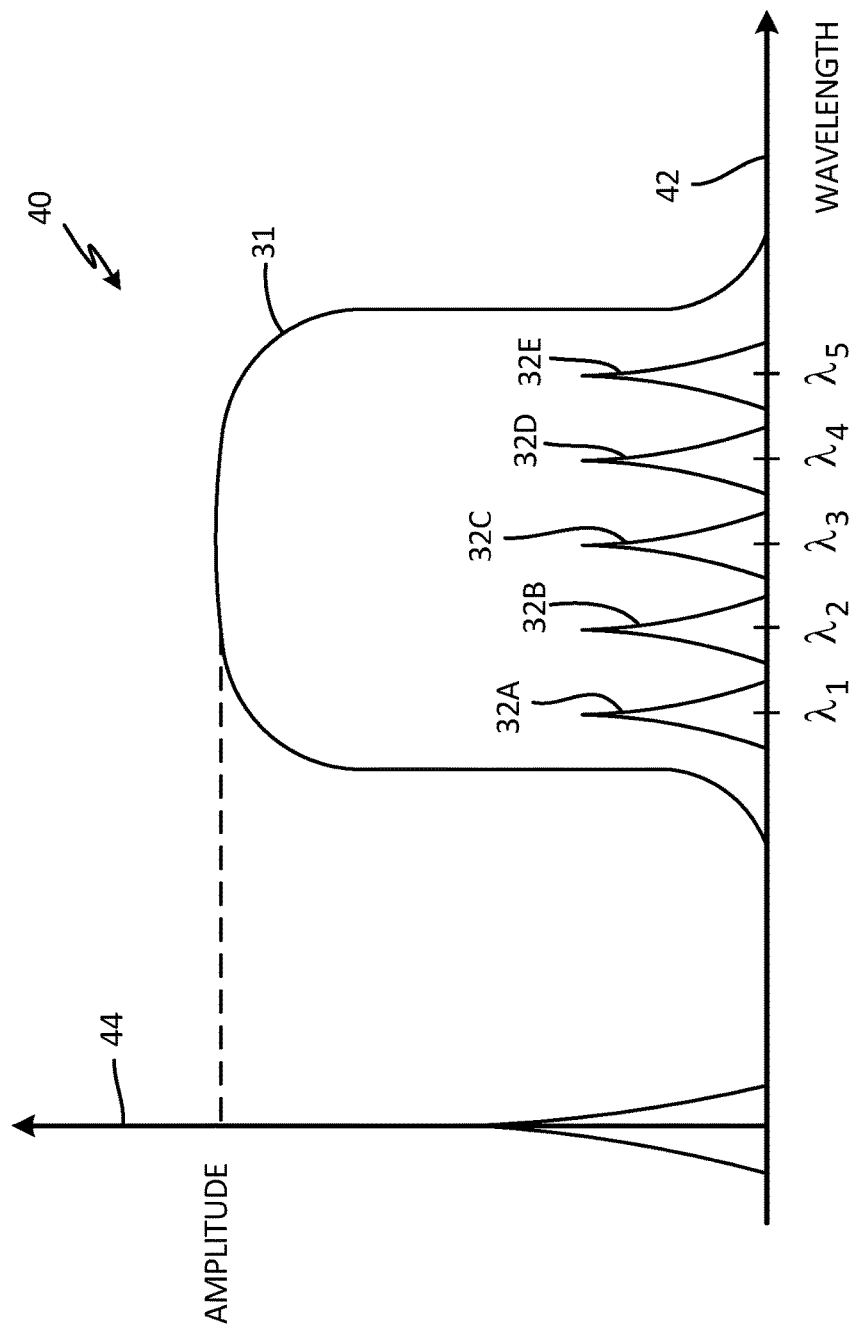
FIG. 3 is a graph depicting frequency spectra of the emitted pulse and reflected portions of the emitted pulse.

FIG. 3 is a graph depicting frequency spectra of an emitted pulse and of portions reflected by optical sensors. In FIG. 3, graph 40 has horizontal axis 42 and vertical axis 44. Horizontal axis 42 is indicative of wavelength of optical energy. Vertical axis 44 is indicative of amplitude of optical energy. Graph 40 depicts amplitude-wavelength relations corresponding to pulse 31 of optical energy emitted by optical emitter 18 (depicted in FIG. 1) and portions 32A-32E reflected by each of optical acoustic sensors $S_1$-$S_5$, respectively. Optical acoustic sensors $S_1$-$S_5$ have different spatial frequencies of fiber Bragg gratings from one another, as indicated on graph 40 by wavelengths $\lambda_1$-$\lambda_5$, respectively. In some embodiments, acoustic condition of aircraft structure 11 is indicated by amplitude variation of reflected portions 32A-3E. In some embodiments, acoustic condition of aircraft structure 11 is indicated by wavelength variation of reflected portions 32A-32E.

Figure 4:
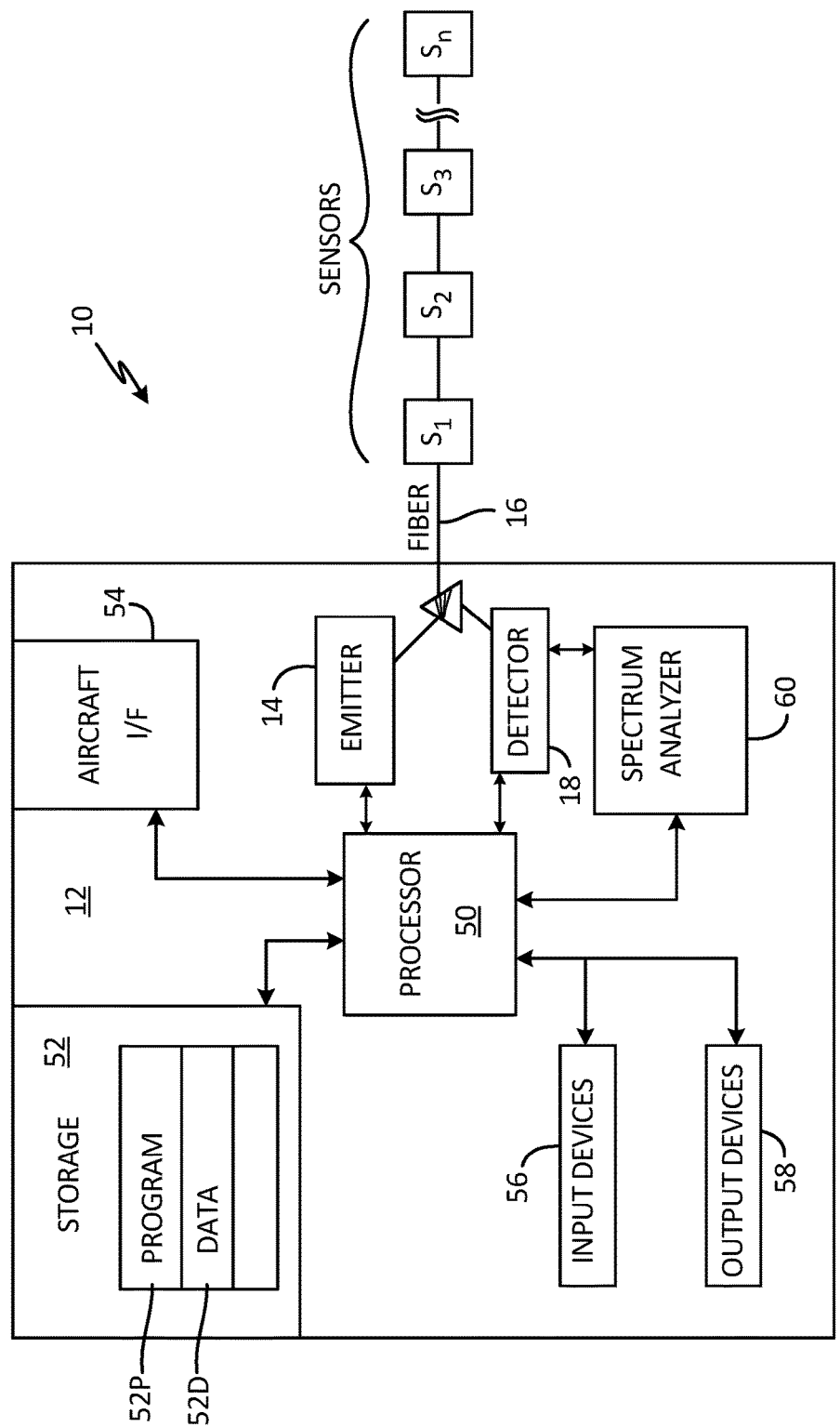
FIG. 4 is a block diagram of an exemplary distributed acoustic event monitoring system.

FIG. 4 is a block diagram of an exemplary distributed acoustic event monitoring system. In FIG. 4, distributed acoustic event monitoring system 10 includes controller 12, optical emitter 14, optical fiber network 16, optical detector 18, and sensors $S_1$-$S_N$. Sensors $S_1$-$S_N$ are located at various sensor locations along optical fiber network 16. Each of sensors $S_1$-$S_N$ can be external to optical fiber network 16 or can be formed within optical fiber network 16. Each of sensors $S_1$-$S_N$ can generate and/or affect an optical signal in response to a physical parameter.

Controller 12 includes processor(s) 50, optical emitter 14, optical detector 18, storage device(s) 52, aircraft interface 54, input devices 56, output devices 58 and spectrum analyzer 60. Processor(s) 50 can receive program instructions 52P from storage device(s) 52. Processor(s) 50 can be configured to control distributed acoustic event monitoring system 10, based on received program instructions 52P. For example processor(s) 50 can be configured to cause optical emitter 14 to generate an optical signal and/or a pulse of optical energy. The generated optical signal is directed into optical fiber network 16 where it is transmitted to sensors $S_1$-$S_N$. Optical sensors $S_1$-$S_N$ can be configured to generate narrow-band optical signals in response to the transmitted optical signal. For example, one or more of the sensors $S_1$-$S_N$ can be a fiber Bragg grating. The fiber Bragg grating can generate reflect a narrow-band portion of the transmitted optical signal. The reflected narrow-band portion of the reflected optical signal can have a wavelength $\lambda$ that is indicative of a physical parameter. One or more of the sensors $S_1$-$S_N$ can be a Fabry Pérot interferometer, for example. Each of the Fabry Pérot interferometers can generate a narrow-band light signal and transmit it to optical fiber network 16.

Optical detector 18 can detect the narrow-band optical signals generated by sensors $S_1$-$S_N$. The timing at which the narrow-band optical signals (relative to the transmitted optical signal or some other timing metric) generated by sensors $S_1$-$S_N$ are received by optical emitter/detector module can be indicative of the specific sensor of sensors $S_1$-$S_N$ that generated the received narrow-band optical signals. Spectrum analyzer 60 can be configured to determine a wavelength of narrow-band optical signals generated by sensors $S_1$-$S_N$ and detected by optical detector 18. Various types of spectrum analyzers 60 can be used for such a determination of wavelength.

Processor(s) 50 receives, from optical detector 18, output signals indicative of amplitude of portions 32A-32E generated by sensors $S_1$-$S_N$. Processor(s) 50 receives, from spectrum analyzer 60, output signals indicative of determined wavelengths $\lambda_1$-$\lambda5$ of narrow-band optical signals generated by sensors $S_1$-$S_N$. Processor(s) 50 can associate the determined wavelength $\lambda_1$-$\lambda_N$ with acoustic condition corresponding to those sensed by the sensors $S_1$-$S_N$. Processor(s) 50 can compare the acoustic conditions with predetermined thresholds to determine if the sensed acoustic conditions fall within a normal and/or expected range of values. If, for example, one or more of the acoustic conditions does not fall within the expected range of values, processor(s) 50 can generate an alert signal and send the generated alert signal to aircraft interface 54. In some embodiments, processor(s) 50 can store and/or log the associated parameter values in data memory 52D. In some embodiments, processor(s) 50 may interface with other input and output devices 56 and 58.

As illustrated in FIG. 5, controller 12 includes processor(s) 50, optical emitter 14, optical detector 18, storage device(s) 52, aircraft interface 54, user input devices 56, user output devices 58, and spectrum analyzer 60. However, in certain examples, controller 12 can include more or fewer components. For instance, in examples where controller 12 is an avionics unit, controller 12 may not include user input devices 56 and/or user output devices 58. In some examples, such as where controller 12 is a mobile or portable device such as a laptop computer, controller 12 may include additional components such as a battery that provides power to components of controller 12 during operation.

Processor(s) 50, in one example, is configured to implement functionality and/or process instructions for execution within controller 12. For instance, processor(s) 50 can be capable of processing instructions stored in storage device(s) 52. Examples of processor(s) 50 can include any one or more of a microprocessor, a controller, a digital signal processor(s) (DSP), an application specific integrated circuit (ASIC), a field-programmable gate array (FPGA), or other equivalent discrete or integrated logic circuitry.

Storage device(s) 52 can be configured to store information within controller 12 during operation. Storage device(s) 52, in some examples, is described as computer-readable storage media. In some examples, a computer-readable storage medium can include a non-transitory medium. The term "non-transitory" can indicate that the storage medium is not embodied in a carrier wave or a propagated signal. In certain examples, a non-transitory storage medium can store data that can, over time, change (e.g., in RAM or cache). In some examples, storage device(s) 52 is a temporary memory, meaning that a primary purpose of storage device(s) 52 is not long-term storage. Storage device(s) 52, in some examples, is described as volatile memory, meaning that storage device(s) 52 do not maintain stored contents when power to controller 12 is turned off. Examples of volatile memories can include random access memories (RAM), dynamic random access memories (DRAM), static random access memories (SRAM), and other forms of volatile memories. In some examples, storage device(s) 52 is used to store program instructions for execution by processor(s) 50. Storage device(s) 52, in one example, is used by software or applications running on controller 12 (e.g., a software program implementing long-range cloud conditions detection) to temporarily store information during program execution.

Storage device(s) 52, in some examples, can also include one or more computer-readable storage media. Storage device(s) 52 can be configured to store larger amounts of information than volatile memory. Storage device(s) 52 can further be configured for long-term storage of information. In some examples, storage device(s) 52 include non-volatile storage elements. Examples of such non-volatile storage elements can include magnetic hard discs, optical discs, flash memories, or forms of electrically programmable memories (EPROM) or electrically erasable and programmable (EEPROM) memories.

In some embodiments, controller 12 includes a communications module. The communications modules can be configured to communicate with external devices via one or more networks, such as one or more wireless or wired networks or both. The communications module can be a network interface card, such as an Ethernet card, an optical transceiver, a radio frequency transceiver, or any other type of device that can send and receive information. Other examples of such network interfaces can include Bluetooth, 3G, 4G, and Wi-Fi radio computing devices as well as Universal Serial Bus (USB).

Aircraft interface 54 can be used to communicate information between controller 12 and an aircraft. In some embodiments, such information can include aircraft conditions, flying conditions, and/or atmospheric conditions. In some embodiments, such information can include data processed by controller 12, such as, for example, alert signals. Aircraft interface 54 can also include a communications module. Aircraft interface 54, in one example, utilizes the communications module to communicate with external devices via one or more networks, such as one or more wireless or wired networks or both. The communications module can be a network interface card, such as an Ethernet card, an optical transceiver, a radio frequency transceiver, or any other type of device that can send and receive information. Other examples of such network interfaces can include Bluetooth, 3G, 4G, and Wi-Fi radio computing devices as well as Universal Serial Bus (USB). In some embodiments, communication with the aircraft can be performed via a communications bus, such as, for example, an Aeronautical Radio, Incorporated (ARINC) standard communications protocol. In an exemplary embodiment, aircraft communication with the aircraft can be performed via a communications bus, such as, for example, a Controller Area Network (CAN) bus.

User input devices 56, in some examples, are configured to receive input from a user. Examples of user input devices 56 can include a mouse, a keyboard, a microphone, a camera device, a presence-sensitive and/or touch-sensitive display, push buttons, arrow keys, or other type of device configured to receive input from a user. In some embodiments, input communication from the user can be performed via a communications bus, such as, for example, an Aeronautical Radio, Incorporated (ARINC) standard communications protocol. In an exemplary embodiment, user input communication from the user can be performed via a communications bus, such as, for example, a Controller Area Network (CAN) bus.

User output devices 58 can be configured to provide output to a user. Examples of user output devices 58 can include a display device, a sound card, a video graphics card, a speaker, a cathode ray tube (CRT) monitor, a liquid crystal display (LCD), a light emitting diode (LED) display, an organic light emitting diode (OLED) display, or other type of device for outputting information in a form understandable to users or machines. In some embodiments, output communication to the user can be performed via a communications bus, such as, for example, an Aeronautical Radio, Incorporated (ARINC) standard communications protocol. In an exemplary embodiment, output communication to the user can be performed via a communications bus, such as, for example, a Controller Area Network (CAN) bus.

The following are non-exclusive descriptions of possible embodiments of the present invention.

Apparatus and associated methods relate to a system for monitoring an aircraft structure. The system includes an optical fiber network extending along an aircraft structure. The system includes an optical emitter optically coupled to the optical fiber network and configured to generate an optical signal and to transmit the generated optical signal to the optical fiber network. The system includes a series of optical acoustic transducers optically coupled to the optical fiber network and mechanically coupled to the aircraft structure at a series of acoustic sensor locations. Each of the series of optical acoustic transducers is configured to receive the generated optical signal, to generate an optical response signal indicative of a detected acoustic condition at a respective acoustic sensor location, and to transmit the generated optical response signal to the optical fiber network. The system includes an optical detector optically coupled to the optical fiber network and configured to receive the transmitted optical response signals generated by the series of optical acoustic transducers. The system also includes a controller configured to generate a trigger signal, if a triggering one of the received optical response signals is indicative of a triggering acoustic event. The controller is further configured to determine, based on a relative timing of the triggering one of the received optical response signals, a specific one of the acoustic sensor locations associated with a specific one of the series of optical acoustic transducers that generated the triggering one of the optical response signals associated with the generated trigger signal.

The system of the preceding paragraph can optionally include, additionally and/or alternatively, any one or more of the following features, configurations and/or additional components:

A further embodiment of the foregoing system can further include a Health & Usage Monitoring System (HUMS) configured to receive the trigger signal and to perform, in response to receiving the trigger signal, a health scan of the aircraft structure at the specific one of the series of acoustic sensor locations.

A further embodiment of any of the foregoing systems, wherein the HUMS can include a mechanical diagnostics engine configured to actively monitor acoustic signals and to compare the monitored acoustic signals to a baseline acoustic signal.

A further embodiment of any of the foregoing systems, wherein the optical signal generated by the optical emitter can have optical energy spanning a domain of wavelengths.

A further embodiment of any of the foregoing systems, wherein each of the series of optical acoustic transducers can be a Fiber Bragg Grating (FBG) within the optical fiber network.

A further embodiment of any of the foregoing systems, wherein each of the series of FBGs within the optical fiber can have a different spatial frequency from others of the FBGs, so as to reflect a different subdomain of wavelengths of the domain of wavelengths spanned by the optical signal generated by the optical emitter.

A further embodiment of any of the foregoing systems, wherein the optical fiber network can include a series of optical fibers. Each of the series of optical acoustic transducers can be optically coupled to a corresponding one of the optical fiber.

A further embodiment of any of the foregoing systems, wherein the aircraft structure is a wing.

A further embodiment of any of the foregoing systems can further include a Structural Health Monitoring (SHM) system configured to receive the trigger signal and to perform, in response to receiving the trigger signal, a health scan of the aircraft structure at the specific one of the series of acoustic sensor locations.

A further embodiment of any of the foregoing systems, wherein the SHM system can be configured to actively generate acoustic signals, to detect acoustic responses to the actively generated acoustic signals, and to compare the detected acoustic responses with a baseline response.

A further embodiment of any of the foregoing systems can further include an optical temperature transducer coupled to the aircraft structure at a temperature sensor location. The optical temperature transducer can be configured to detect a temperature, to generate an optical signal indicative of the detected temperature, and to transmit the generated optical signal to the optical fiber network.

In some embodiments, apparatus and associated methods relate to a method for monitoring the health of an aircraft. The method includes extending an optical fiber network along an aircraft structure. The method includes generating an optical signal. The method includes transmitting the generated optical signal to the optical fiber network. The method includes detecting, via a series of optical acoustic transducers mechanically coupled to the aircraft structure at a series of acoustic sensor locations along the optical fiber network, acoustic conditions at the series of acoustic sensor locations. The method includes receiving, via the series of optical acoustic transducers, the transmitted optical signal. The method includes generating, in response to receiving the transmitted optical signal via the series of optical acoustic transducers, optical response signals indicative of the detected acoustic conditions. The method includes transmitting, via the series of optical acoustic transducers, the generated optical response signals to the optical fiber network. The method includes receiving, via an optical detector, the transmitted optical signals. The method includes generating, via a controller, a trigger signal, if a triggering one of the received optical response signals is indicative of a triggering acoustic event. The method also determining, based on a relative timing of the triggering one of the received optical response signals via the controller, a specific one of the acoustic sensor locations associated with a specific one of the series of optical acoustic transducers that generated the triggering one of the optical response signals associated with the generated trigger signal.

The method of the preceding paragraph can optionally include, additionally and/or alternatively, any one or more of the following steps, features, configurations and/or additional components:

A further embodiment of the foregoing method can further include receiving, via a Health & Usage monitoring system (HUMS), the trigger signal.

A further embodiment of any of the foregoing methods can further include performing, by the HUMS in response to receiving the received trigger signal, a health scan of the aircraft structure at the specific one of the series of acoustic sensor locations.

A further embodiment of any of the foregoing methods can further include actively generating, via a Structural Health Monitoring (SHM) system, acoustic signals.

A further embodiment of any of the foregoing methods can further include sensing, via the SHM system, acoustic responses to the actively generated acoustic signals.

A further embodiment of any of the foregoing methods can further include comparing, via the SHM system, the sensed acoustic responses to a baseline response.

A further embodiment of any of the foregoing methods, wherein the generated optical signal can have optical energy spanning a domain of wavelengths.

A further embodiment of any of the foregoing methods, wherein generating optical response signals indicative of the detected acoustic conditions can include reflecting, via a series of Fiber Bragg Gratings (FBGs), portions of the transmitted optical signal from within the optical fiber network.

A further embodiment of any of the foregoing methods, wherein each of the FBGs can have a different spatial frequency from the others, so as to reflect a different subdomain of wavelengths of the domain of wavelengths spanned by the optical signal generated by the optical emitter.

A further embodiment of any of the foregoing methods, wherein the aircraft structure can be a wing, and or an engine nacelle.

A further embodiment of any of the foregoing methods can further include detecting, via an optical temperature transducer coupled to the aircraft structure at a temperature sensor location, a temperature.

A further embodiment of any of the foregoing methods can further include receiving, via the optical temperature transducers, the transmitted optical signal.

A further embodiment of any of the foregoing methods can further include generating, in response to receiving the transmitted optical signal via the optical temperature transducer, an optical response signal indicative of the detected temperature.

A further embodiment of any of the foregoing methods can further include transmitting the generated optical response signal to the optical fiber network.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A system for monitoring an aircraft structure, the system comprising:
   an optical fiber network extending along an aircraft structure;
   an optical emitter optically coupled to the optical fiber network and configured to generate an optical signal and to transmit the generated optical signal to the optical fiber network;
   a series of optical acoustic transducers optically coupled to the optical fiber network and mechanically coupled to the aircraft structure at a series of acoustic sensor locations, each of the series of optical acoustic transducers configured to receive the generated optical signal, to generate an optical response signal indicative of a detected passive acoustic condition at a respective acoustic sensor location, and to transmit the generated optical response signal to the optical fiber network;
   an optical detector optically coupled to the optical fiber network and configured to receive the transmitted optical response signals generated by the series of optical acoustic transducers; and
   a controller configured to generate a trigger signal configured to trigger an active health monitor scan, if a triggering one of the received optical response signals is indicative of a triggering acoustic event, the controller further configured to determine, based on a relative timing of the triggering one of the received optical response signals, a specific one of the acoustic sensor locations associated with a specific one of the series of optical acoustic transducers that generated the triggering one of the optical response signals associated with the generated trigger signal.

2. The system of claim 1, further comprising a Health & Usage Monitoring System (HUMS) configured to receive the trigger signal and to perform, in response to receiving the trigger signal, a health scan of the aircraft structure at the specific one of the series of acoustic sensor locations.

3. The system of claim 2, wherein the HUMS comprises:
   a mechanical diagnostics engine configured to actively monitor acoustic signals and to compare the monitored acoustic signals to a baseline acoustic signal.

4. The system of claim 3, wherein each of the series of optical acoustic transducers is a Fiber Bragg Grating (FBG) within the optical fiber network.

5. The system of claim 1, wherein the optical signal generated by the optical emitter has optical energy spanning a domain of wavelengths.

6. The system of claim 5, wherein each of the series of FBGs within the optical fiber has a different spatial frequency from others of the FBGs, so as to reflect a different subdomain of wavelengths of the domain of wavelengths spanned by the optical signal generated by the optical emitter.

7. The system of claim 1, wherein the optical fiber network comprises a series of optical fibers, and wherein each of the series of optical acoustic transducers is optically coupled to a corresponding one of the optical fiber.

8. The system of claim 1, wherein the aircraft structure is a wing.

9. The system of claim 1, further comprising a Structural Health Monitoring (SHM) system configured to receive the trigger signal and to perform, in response to receiving the trigger signal, a health scan of the aircraft structure at the specific one of the series of acoustic sensor locations.

10. The system of claim 9, wherein the SHM system is configured to actively generate acoustic signals, to detect acoustic responses to the actively generated acoustic signals, and to compare the detected acoustic responses with a baseline response.

11. The system of claim 1, further comprising an optical temperature transducer coupled to the aircraft structure at a temperature sensor location and configured to detect a temperature, to generate an optical signal indicative of the detected temperature, and to transmit the generated optical signal to the optical fiber network.

12. A method for monitoring health of an aircraft structure, the method comprising:
    extending an optical fiber network along an aircraft structure;
    generating, an optical signal;
    transmitting the generated optical signal to the optical fiber network;
    detecting, via a series of optical acoustic transducers mechanically coupled to the aircraft structure at a series of acoustic sensor locations along the optical fiber network, passive acoustic conditions at the series of acoustic sensor locations;
    receiving, via the series of optical acoustic transducers, the transmitted optical signal;
    generating, in response to receiving the transmitted optical signal via the series of optical acoustic transducers, optical response signals indicative of the detected passive acoustic conditions;
    transmitting, via the series of optical acoustic transducers, the generated optical response signals to the optical fiber network;
    receiving, via an optical detector, the transmitted optical signals;
    generating, via a controller, a trigger signal configured to trigger an active health monitor scan, if a triggering one of the received optical response signals is indicative of a triggering acoustic event; and
    determining, based on a relative timing of the triggering one of the received optical response signals via the controller, a specific one of the acoustic sensor locations associated with a specific one of the series of optical acoustic transducers that generated the triggering one of the optical response signals associated with the generated trigger signal.

13. The method of claim 12, further comprising:
    receiving, via a Health & Usage monitoring system (HUMS), the trigger signal; and
    performing, by the HUMS in response to receiving the received trigger signal, a health scan of the aircraft structure at the specific one of the series of acoustic sensor locations.

14. The method of claim 12, further comprising:
    actively generating, via a Structural Health Monitoring (SHM) system, acoustic signals;
    sensing, via the SHM system, acoustic responses to the actively generated acoustic signals; and
    comparing, via the SHM system, the sensed acoustic responses to a baseline response.

15. The method of claim 12, wherein the generated optical signal has optical energy spanning a domain of wavelengths.

16. The method of claim 15, wherein generating optical response signals indicative of the detected acoustic conditions comprises:

reflecting, via a series of Fiber Bragg Gratings (FBGs), portions of the transmitted optical signal from within the optical fiber network.

17. The method of claim 16, wherein each of the FBGs has a different spatial frequency from the others, so as to reflect a different subdomain of wavelengths of the domain of wavelengths spanned by the optical signal generated by the optical emitter.

18. The method of claim 12, wherein the aircraft structure is a wing.

19. The method of claim 12, wherein the aircraft structure is an engine nacelle.

20. The method of claim 12, further comprising:

detecting, via an optical temperature transducer coupled to the aircraft structure at a temperature sensor location, a temperature;

receiving, via the optical temperature transducers, the transmitted optical signal;

generating, in response to receiving the transmitted optical signal via the optical temperature transducer, an optical response signal indicative of the detected temperature; and transmitting the generated optical response signal to the optical fiber network.

\* \* \* \* \*